United States Patent [19]

Tuman

[11] Patent Number: 5,205,832
[45] Date of Patent: Apr. 27, 1993

[54] ENDO-TRACHEAL TUBE SUPPORT DEVICE

[76] Inventor: David H. Tuman, 5001 Miners Ranch Rd., Ordville, Calif. 95966

[21] Appl. No.: 881,305

[22] Filed: May 7, 1992

Related U.S. Application Data

[63] Continuation of Ser. No. 505,560, Apr. 6, 1990, abandoned.

[51] Int. Cl.$^5$ .............................................. A61M 5/32
[52] U.S. Cl. ............................ 604/179; 128/DIG. 26; 128/912
[58] Field of Search ............... 604/178, 179, 180, 174, 604/177; 128/DIG. 26, 911, 912, 200.26, 200.17

[56] References Cited

U.S. PATENT DOCUMENTS

| | | | |
|---|---|---|---|
| 3,713,448 | 1/1973 | Arrott | 128/DIG. 26 |
| 3,730,187 | 5/1973 | Reynolds | 604/178 |
| 4,088,136 | 4/1978 | Hasslinger et al. | 604/179 |
| 4,331,144 | 5/1982 | Wapner | 128/DIG. 26 |
| 4,378,012 | 3/1983 | Brown | 128/DIG. 26 |
| 4,658,814 | 4/1987 | Anderson | 528/DIG. 26 |
| 4,822,342 | 4/1989 | Browner | 604/180 |

*Primary Examiner*—C. Fred Rosenbaum
*Assistant Examiner*—Chalin Smith
*Attorney, Agent, or Firm*—Limbach & Limbach

[57] ABSTRACT

An endo-tracheal tube support apparatus is disclosed which includes a predetermined length of tubing having an oblong cross section and an aperture formed at a point along the length of tubing; and strap means positionable about the face and back of head of the patient, a portion of which is threaded through the length of tubing, for securing the tubing in the vicinity of the patient's nose or mouth, wherein a portion of the strap means protrudes through the aperture to form a loop for capturing the endo-tracheal tube. In preferred embodiments of the present invention, the aperture is positioned in a rounded edge of the tube in the form of a semicircular notch. The loop portion includes a section of double sided sticky tape with a pull tab. When the tab is pulled, the sticky surface of the tape is exposed and is used to prevent the endo-tracheal tube from slipping. Tightening of the strap means causes the loop portion to urge the endo-tracheal tube against the notch to seat the tube more securely in the notch and to apply additional friction to the endo-tracheal tube. A quick release buckle is employed along with hook and loop patches to permit easy adjustments of the length of the strap means.

15 Claims, 2 Drawing Sheets

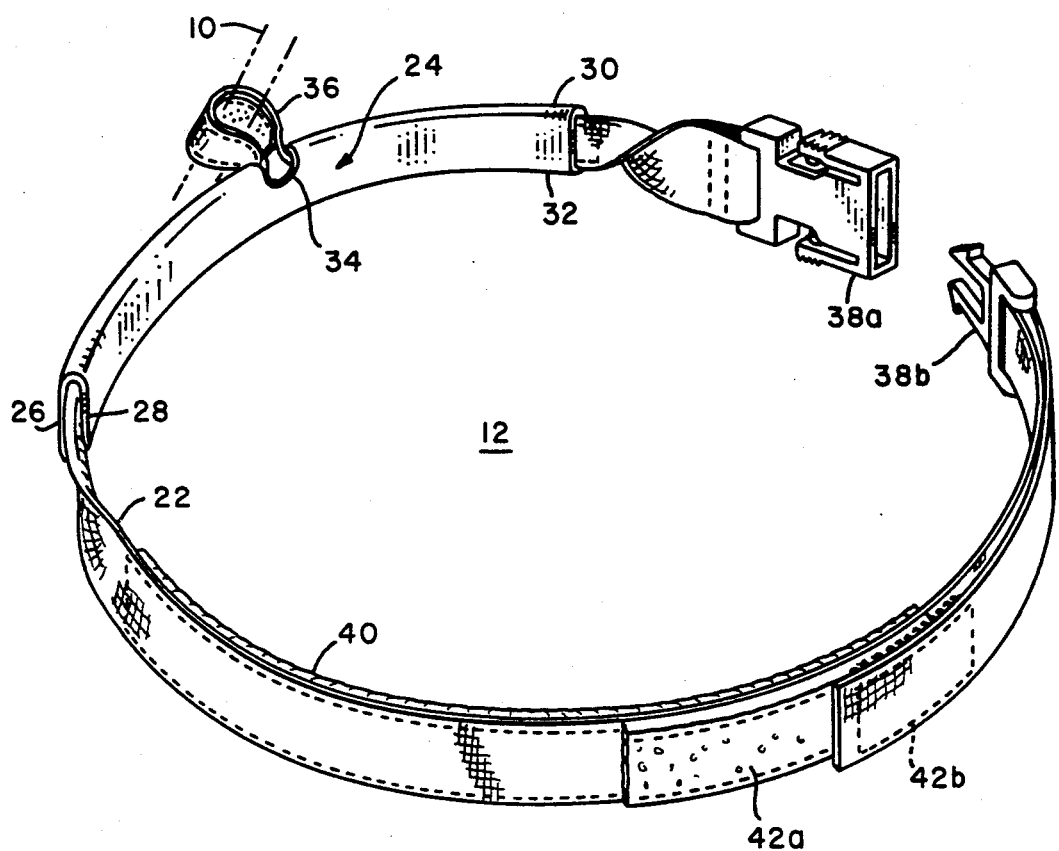
FIG. 1.
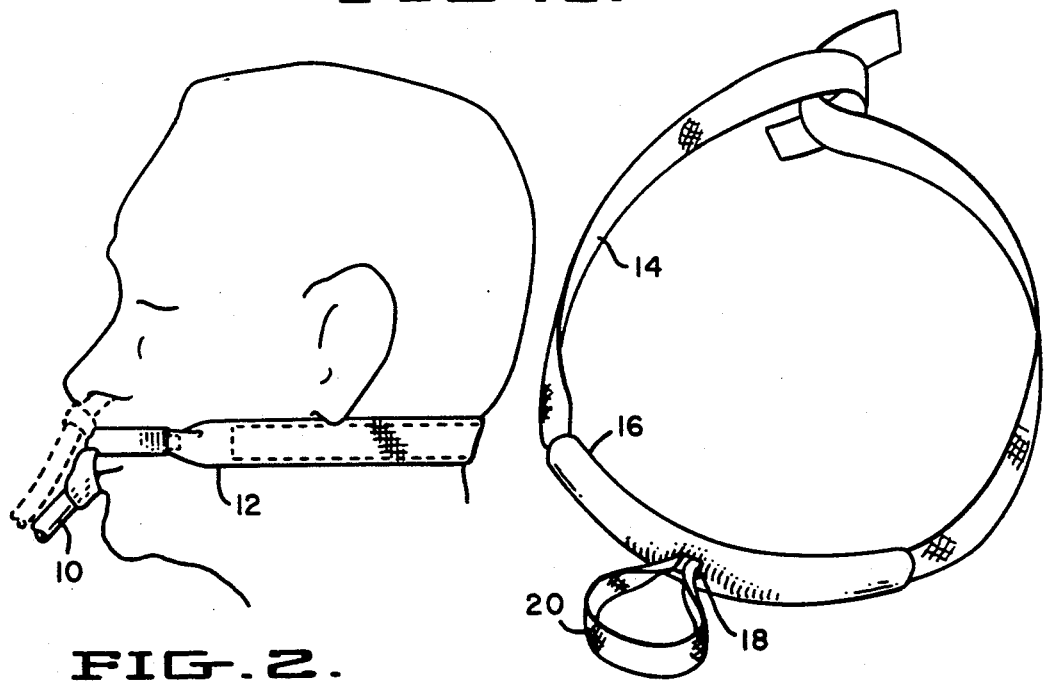
FIG. 2.
FIG. 3. (PRIOR ART)

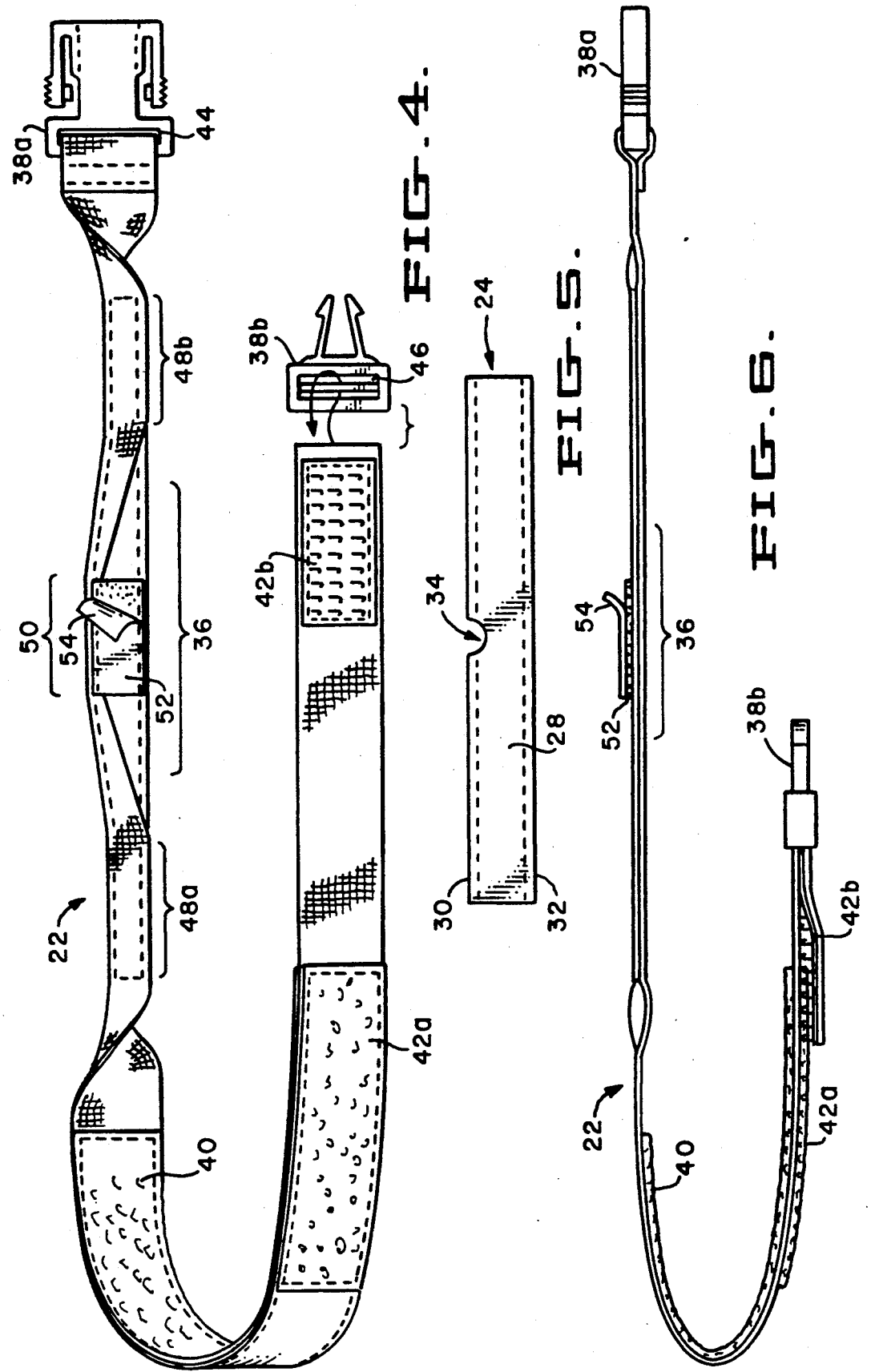

ENDO-TRACHEAL TUBE SUPPORT DEVICE

This is a continuation of co-pending application Ser. No. 07/505,560 filed on Apr. 6, 1990.

TECHNICAL FIELD

The present invention is directed generally to structures for supporting endo-tracheal tubes; and more specifically to a device which fits around the face and head of a patient, is quickly attached or released, and is easily adjustable.

BACKGROUND ART

In patient care scenarios it is sometimes necessary to insert an endo-tracheal tube through a patient's nose or mouth, into the wind pipe, and then into the patient's lungs in order to administer air/oxygen from a T-tube, bag-mask device, or a continuous respiratory ventilation device. In many instances, the tube is kept from moving by placing tape around the endo-tracheal tube and onto the skin of the patient's face and head. Such a practice has several disadvantages such as causing blistering and eroding of the patient's skin, as well as causing rips an tears in the gloves of the medical personnel treating the patient.

Several attempts have been made to provide an improved endo-tracheal tube support device. Several of these prior approaches include the use of a length of rubber having fabric ties at each end, which is used by wrapping the length of rubber around the tube and using the fabric ties to secure the device around the head of the patient; a length of fabric having a portion wrapped with a cellophane type plastic and including a length of wire of shaping the curvature of the cellophane section.

Another approach involves the use of a length of foam stretch rubber having ties at the ends with sticky surfaces. The stretch rubber passes around the back of the head and the ties are secured around the endo-tracheal tube. Still another approach uses a circular structure for capturing the endo-tracheal tube, connected by plastic tubes to a length of broad cloth. The broad cloth is the placed around the patient's head and tied-off.

A previous approach used by the inventor in the subject application involved a length of plastic tubing having a circular cross section and a square aperture positioned at some point along the plastic tubing. A length of broad cloth was threaded through the plastic tubing, and a portion of the broad cloth was pulled through the square aperture to form a loop for capturing the endo-tracheal tube. The ends of the broad cloth were tied off at the back of the patient's head.

All of the above approaches have several disadvantages such as slippage; difficulty of adequately tying off the ends; and difficulty in adjustment.

SUMMARY OF THE INVENTION

The above problems and disadvantages of prior endo-tracheal tube support devices are overcome by the present invention of an apparatus comprising a predetermined length of tubing having an oblong cross section and an aperture formed at a point along the length of tubing; and strap means positionable about the face and back of head of the patient, a portion of which is threaded through the length of tubing, for securing the tubing in the vicinity of the patient's nose or mouth, wherein a portion of the strap means protrudes through the aperture to form a loop for capturing the endo-tracheal tube.

In preferred embodiments of the present invention, the aperture is positioned in a rounded edge of the tube in the form of a semi-circular notch. The loop portion includes a section of double sided sticky tape with a pull tab. When the tab is pulled, the sticky surface of the tape is exposed and is used to prevent the endo-tracheal tube from slipping. A quick release buckle is employed along with hook and loop patches to permit easy adjustments of the length of the strap means.

It is therefore an object of the present invention to provide an endo-tracheal tube support device which is easy to use and adjust.

It is another object of the present invention to provide an endo-tracheal tube support device which employs an elongated portion of flat tubing having a semi-circular notch in one edge.

It is a further object of the present invention to provide an endo-tracheal tube support device which has an adjustable length, a quick-release securing mechanism.

These and other features and advantages of the present invention will be more readily understood upon consideration of the following detailed description of the present invention and accompanying drawings.

BRIEF DESCRIPTION OF THE DRAWINGS

FIG. 1 is a perspective view of the present invention.

FIG. 2 illustrates the present invention as it is used to secure an endo-tracheal tube in the vicinity of a patient's nose or mouth.

FIG. 3 illustrates a prior art endo-tracheal tube supporting structure invented by the inventor of the present invention.

FIG. 4 provides a detailed illustration of the strap portion of the present invention.

FIG. 5 is a side view of the elongated flat tubing employed in the present invention.

FIG. 6 is an edge-on view of the strap portion of the present invention.

DETAILED DESCRIPTION OF THE PRESENT INVENTION

Referring to FIG. 2, an endo-tracheal tube 10 is shown secured in the vicinity of a patient's nose or mouth by the endo-tracheal tube supporting device 12 of the present invention.

FIG. 3 illustrates a prior art approach used by the inventor of the present invention. There, a length of broad cloth 14 is threaded through a circular cross-section tube 16. A square aperture 18 is provided in the wall of tube 16 so that a portion of broad cloth 14 can be pulled through. This forms a loop portion 20. In use, the endo-tracheal tube is passed through loop 20, tubing 16 is placed over the philtrum, and the ends of the broad cloth 14 are tied off behind the patient's head.

FIG. 1 shows a perspective view of the endo-tracheal tube supporting device 12 of the present invention. Included are a strap portion 22 and a tube portion 24. The tube portion serves as a moisture guard and is preferably an elongated section of flat tubing. See also FIG. 5. Such tubing has an oblong cross section and is readily available. In the past, such tubing has been used as sheaths for scalpels. The flat tubing can be described as having two parallel sides 26 and 28 joined together at the top and bottom by rounded edge sections, 30 and 32, respectively.

The elongated section of flat tubing 24 has a circular aperture, preferably positioned at about the center thereof. In the preferred embodiment, this aperture is formed by way of a semi-circular notch 34 in one of the rounded edge sections. Preferably, the radius of the semi-circular notch 34 is selected to accommodate the diameter of the endo-tracheal tube 10. It has been found that the semi-circular shape of the notch permits the loop portion 36 to engage more readily with the endo-tracheal tube 10. It has also been found that by locating the aperture 34 at the rounded edge of the flat tubing, there is a more comfortable fit of the apparatus over the patient's face. As a further advantage, with the aperture 34 located on the round edge, the flat tube section 24 can be flipped to accommodate patients without teeth.

Strap portion 22 is threaded through the elongated section of flat tubing 24, and a portion of strap portion 22 is pulled through semi-circular notch 34 to form a loop 36. In use, the endo-tracheal tube 10 (shown in phantom) passes through and is captured by loop 36.

Strap portion 22 includes a quick release buckle 38a and 38b, a cushioning patch 40 and a set of hook and loop patches 42b. Referring to FIGS. 4 and 6, these and other features will be described in greater detail. Preferably, strap portion 22 is constructed of a rayon/nylon mixture material. This provides strength and resistance to moisture.

A quick release buckle 38a and 39b is preferably used, and is attached to the ends of strap portion 22. Portion 38a of the buckle is preferably attached by looping one end of the strap portion through slot 44 and tacking the end back down on strap portion 22, such as by sewing. Portion 39b of the buckle is preferably adjustably attached to strap portion 22. This is accomplished as follows.

Fastened at one end and on the outside face of the strap portion 22 is a patch of hook and loop material 42b. Fastened on the outside face, at a point between the ends of strap portion 22 is a complementary patch of hook and loop material 42a. This hook and loop material is sometimes sold under the trademark Velcro ®.

The end of strap portion 22 to which patch 42b is attached is passed through loop 46 of buckle portion 38b. Patch 42 is then pressed over some part of patch 42a and engages therewith. It is to understood that when a greater length of strap portion 22 is desired, patch 42b need not be engaged passed in an over/under fashion through loop 46, and patch 42b acts as a stop.

Patch 40 is located on the inside face of strap portion 22, and is preferably constructed of felt like material such as is used to line the insides of sweat shirts and the like. Patch 40 acts as a cushion between the strap portion 22 and the patient's skin.

In the preferred embodiment of the present invention, the section of strap portion 22 that is used to form loop portion 36 is formed by folding the rayon/nylon material in half and tacking the fold together over portions 48a and 48b. In the area 50 in the immediate vicinity of loop portion 36, the rayon/nylon material folded over just at the edge and tacked down, so that almost the full width of the material is provided. This structure permits easier threading of the strap portion 22 through flat tube 24, and also provides better alignment of loop portion 36 with respect to aperture 34.

It is to be noted that loop portion 36 includes a section 52 of double-sided sticky tape which has been sewn onto the rayon/nylon material. Section 52 has a pull tab which when in place protects the sticky surface, and when removed operates to retard movement of the endo-tracheal tube 10.

In use, endo-tracheal tube 10 is passed through loop 36 of the present invention. Flat tubing portion 24 is placed over the patient's philtrum. With pull tab 54 removed, one end of strap portion 22 is pulled with respect to flat tubing portion 24 to engage loop portion 36 and sticky section 52 with the endo-tracheal tube 10. Buckle portion 39b is pulled around and behind the patient's head and engaged with buckle portion 38b. The free-end of strap portion 22 upon which patch 42b is located is pulled to tighten strap portion 22 around the patient's head. If possible, patch 42b is engaged with patch 42b.

The tightness of strap portion 22, as adjusted by pulling on the free-end portion of strap 22, assists in preventing the endo-tracheal tube 10 from slipping. As strap portion 22 is tightened, loop portion 36 urges the tube 10 against notch 34. This acts to seat the tube 10 more securely in notch 34. By seating tube 10 in notch 34, this increases the friction applied to tube 10 and adds to the friction supplied by the sticky section 52.

In an illustrative example of the present invention, strap portion 22 has a total length of approximately 24 inches, excluding quick release buckle 38a/38b. Cushioning patch 40 has a length of approximately seven inches. Patch portion 42b has a length of approximately one and a quarter inches. Patch portion 42a has a length of approximately four inches. Flat tubing portion 24 has a length of approximately five and a half inches, and a width of approximately one half inch. Notch 34 has a radius of approximately 3/16 inch. This notch size can accommodate endo-tracheal tube sizes from 6 through 11. A length of approximately ⅜ inch of double sided sticky tape is used of section 52.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

I claim:

1. An apparatus for supporting an endo-tracheal tube in the vicinity of a patient's nose or mouth, comprising a predetermined length of tubing having two parallel sides extending over substantially the entire length of tubing, which are joined together at the top and bottom by rounded edge sections to provide a substantially uniform oblong cross section over substantially the entire length of tubing prior to being positioned on the patient, and an aperture formed in one of the rounded edge sections along the length of tubing; and strap means positionable about the face and back of head of an patient, a portion of which is threaded through the length of tubing, for securing the tubing in the vicinity of the patient's nose or mouth, wherein a portion of the strap means protrudes through the aperture to form a loop for capturing the endo-tracheal tube.

2. The apparatus of claim 1, wherein the aperture has a curved shape.

3. The apparatus of claim 1, wherein the aperture extends into the parallel sides of the tubing to form a semi-circular notch.

4. The apparatus of claim 1, further including means positioned in the loop of the strap means for providing a sticky surface for retarding movement of the endo-tracheal tube when said tube has been captured by the loop in the strap means.

5. The apparatus of claim 4, wherein the means for providing a sticky surface includes removable cover means positioned over the sticky surface to protect it and which can be removed to expose the sticky surface.

6. The apparatus of claim 1, wherein the strap means include an elongated length of material having a first end and a second end; and means secured to the first and second ends of the elongated length of material for releasably securing the first and second ends together.

7. The apparatus of claim 6, wherein the releasably securing means is a quick-release buckle.

8. The apparatus of claim 7, further including means for adjustably securing one of the first or second end of the strap means to the releasably securing means.

9. The apparatus of claim 8, wherein the releasably securing means has a loop at one end, and further wherein the means for adjustably securing means include a first patch of hook and loop material positioned on the one end of the elongated length of material; and an complementary patch of hook and loop material having a length greater than the length of the first patch of hook and loop material and positioned on the elongated length of material, and between the one end and the other end thereof;

wherein the one end of the elongated length of material is passed through the loop of the releasably securing means and the first and complementary patches of hook and loop material are engageable with one another.

10. The apparatus of claim 6, wherein the elongated length of material of the strap means has an inside face and an outside face, and further including an elongated patch of cushioning material.

11. The apparatus of claim 10, wherein said cushioning material is felt.

12. The apparatus of claim 3, wherein the endo-tracheal tube has a predetermined diameter, and the semicircular notch has a radius which is selected to accommodate the diameter of the predetermined endo-tracheal tube.

13. An apparatus for supporting an endo-tracheal tube in the vicinity of a patient's nose or mouth, comprising a predetermined length of tubing having a substantially uniform oblong cross section over substantially the entire length of the tubing, said tubing formed from two parallel sides which are joined at together at the top and bottom by rounded edge sections, and a semicircular notch aperture formed in one of the rounded edge sections at a point along the length of tubing; and strap means positionable about the face and back of head of the patient, a portion of which is threaded through the length of tubing, for securing the tubing in the vicinity of the patient's nose or mouth, wherein a portion of the strap means protrudes to the aperture to form a loop for capturing an endo-tracheal tube and includes a length of double-sided sticky tape fastened in the loop and having a removable, protective pull tab.

14. The apparatus of claim 13, wherein the strap means include an elongated length of material having a first end and a second end; and means secured to the first and second ends of the elongated length of material for releasably securing the first and second ends together.

15. The apparatus of claim 14, wherein the releasably securing means has a loop at one end, and further including the means for adjustably securing one of the first or second ends of the strap means to the releasably securing means, comprising a first patch of hook and loop material positioned on the one end of the elongated length of material; and an complementary patch of hook and loop material having a length greater than the length of the first patch of hook and loop material and positioned on the elongated length of material, and between the one end and the other end thereof;

wherein the one end of the elongated length of material is passed through the loop of the releasably securing means and the first and complementary patches of hook and loop material are engageable with one another.

* * * * *